United States Patent [19]

Turnbull

[11] Patent Number: 5,169,385
[45] Date of Patent: Dec. 8, 1992

[54] SAFETY I. V. DRUG INTRODUCER SET

[76] Inventor: Christopher J. Turnbull, 1134 Summit Ave., St. Paul, Minn. 55105

[21] Appl. No.: 736,700

[22] Filed: Jul. 26, 1991

Related U.S. Application Data

[63] Continuation-in-part of Ser. No. 639,814, Jan. 9, 1991, abandoned, which is a continuation-in-part of Ser. No. 470,746, Jan. 26, 1989, abandoned.

[51] Int. Cl.$^5$ .............................................. A61M 1/00
[52] U.S. Cl. ........................................ 604/32; 604/83; 604/248; 604/256; 251/309
[58] Field of Search ................... 604/30, 32, 83, 175, 604/236, 240, 246, 248, 256, 283, 284; 137/550; 251/309, 312

[56] References Cited

U.S. PATENT DOCUMENTS

| | | | |
|---|---|---|---|
| 4,350,157 | 9/1982 | Hoffa | 604/175 |
| 4,512,364 | 4/1985 | Phillips | 137/375 |
| 4,572,231 | 2/1986 | Kotayama | 137/246.15 |
| 4,654,033 | 3/1987 | Lapeyre et al. | 604/175 |
| 4,804,369 | 2/1989 | Lapeyre et al. | 604/175 |
| 4,807,666 | 2/1989 | Morse | 137/625.47 |

Primary Examiner—C. Fred Rosenbaum
Assistant Examiner—C. Maglione
Attorney, Agent, or Firm—Haugen and Nikolai

[57] ABSTRACT

A safety I.V. drug introducer set for use with a I.V. administration set is described for facilitating the injection of drugs into a primary fluid line without the necessity of an exposed hypodermic needle. In one embodiment, a Tee is inserted in the I.V. line whose cross-portion includes one or more check valves and whose stem portion comprises a socket for receiving the distal end of an outer tuburlar shaft having a pair of oppositely disposed ports passing through the wall thereof near the distal end. Fitted into the lumen of the outer tubular shaft is an inner tubular shaft having but a single aperture at its distal end alignable with one, the other, or neither of the pair of apertures in the outer shaft. A hollow key member is designed to fit within the non-circular bore of the inner tubular shaft for facilitating the rotation thereof. The key member also includes a single aperture at its distal end which is continuously aligned with the single aperture in the inner tubular member. Moreover, a Luer fitting is provided at the proximal end of the key member whereby a conventional syringe may be joined to it. The kit further includes a needleless spike matable with the key member for transferring a liquid from a medicine vial into a syringe. Alternate embodiments are also disclosed.

34 Claims, 14 Drawing Sheets

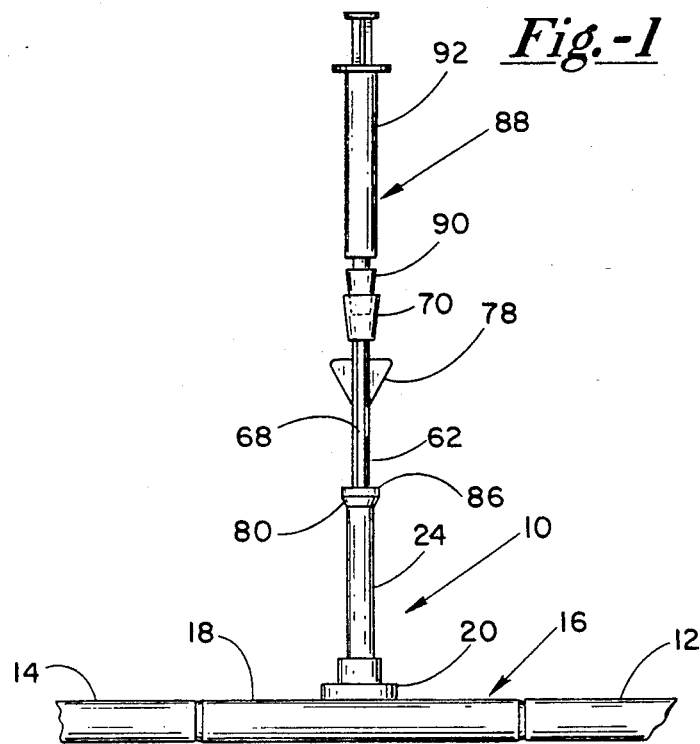
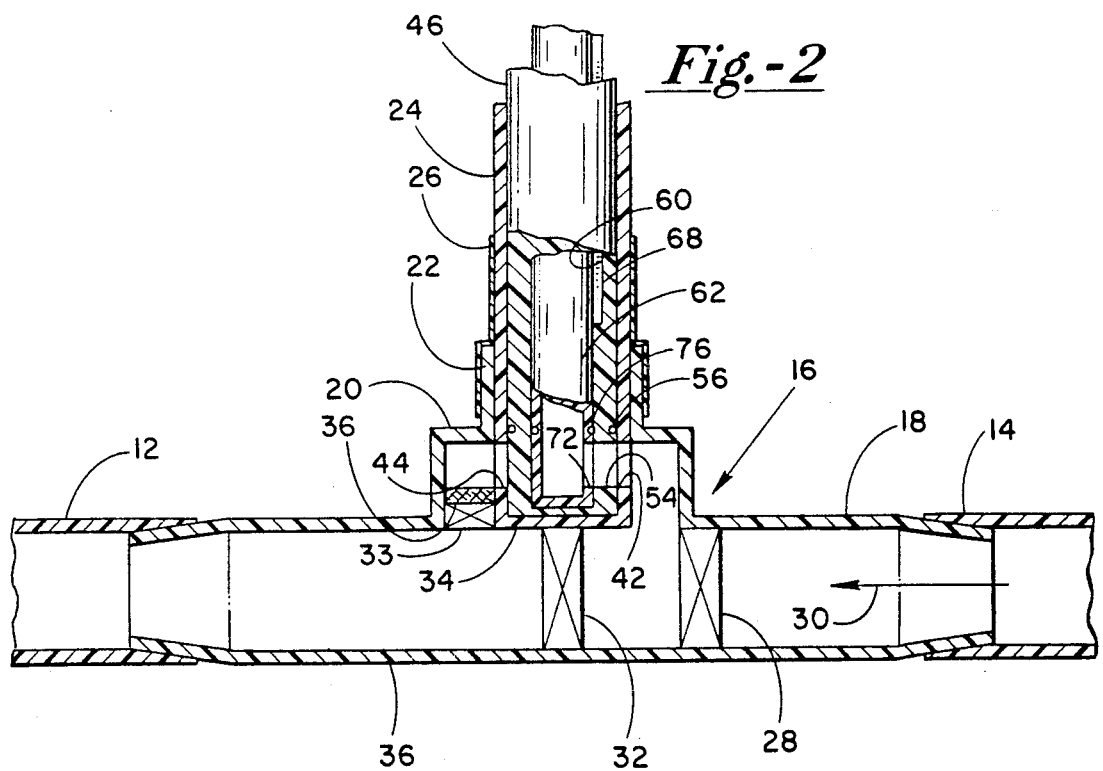

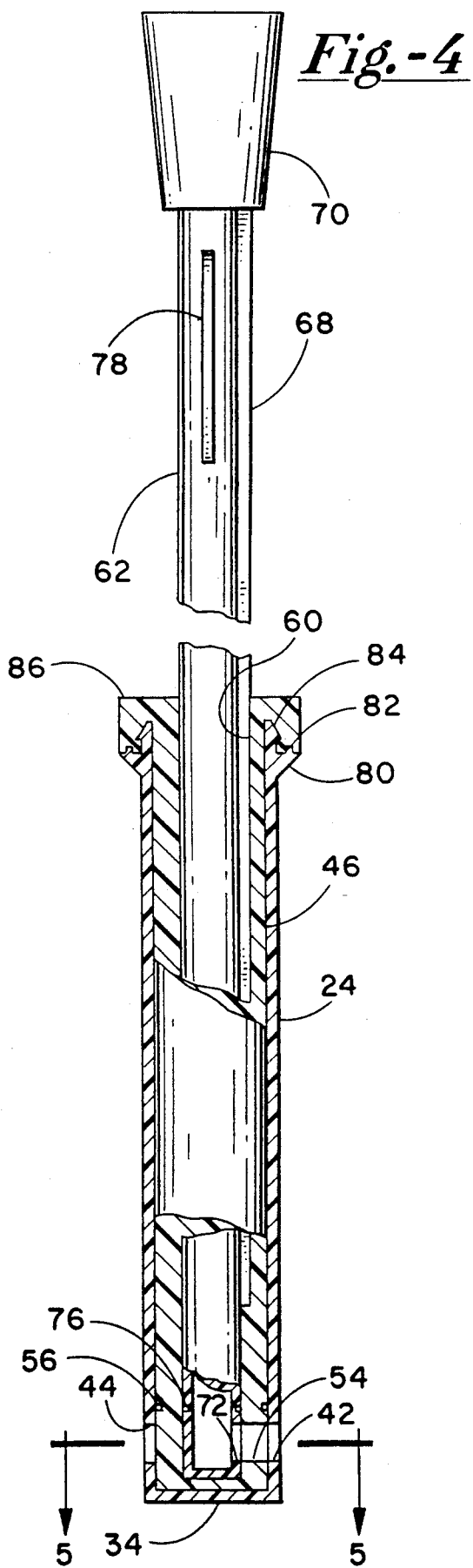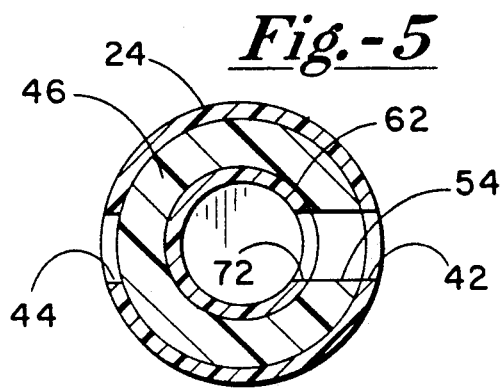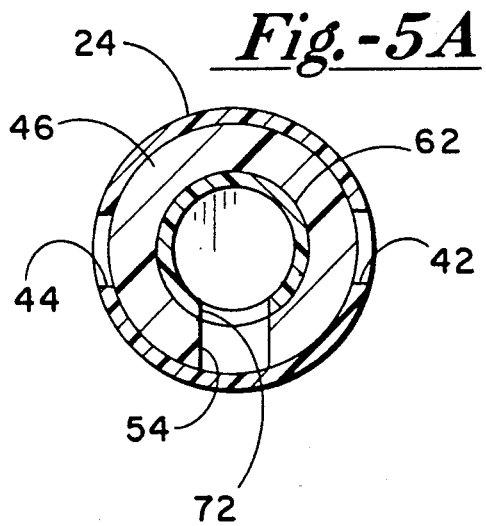

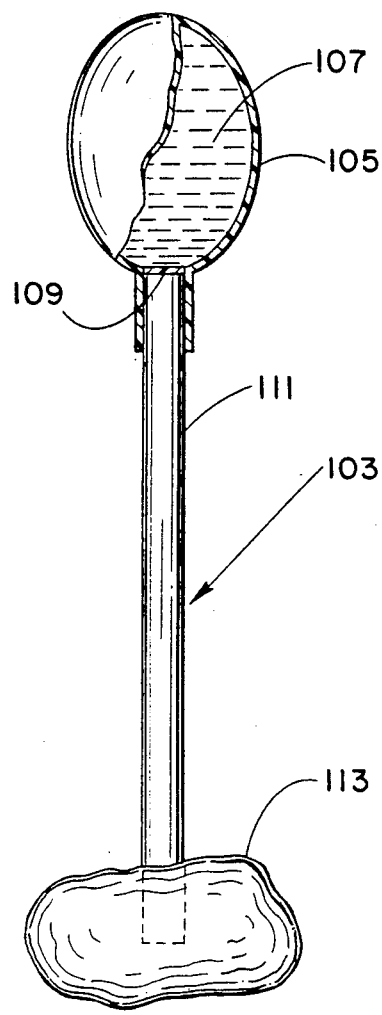
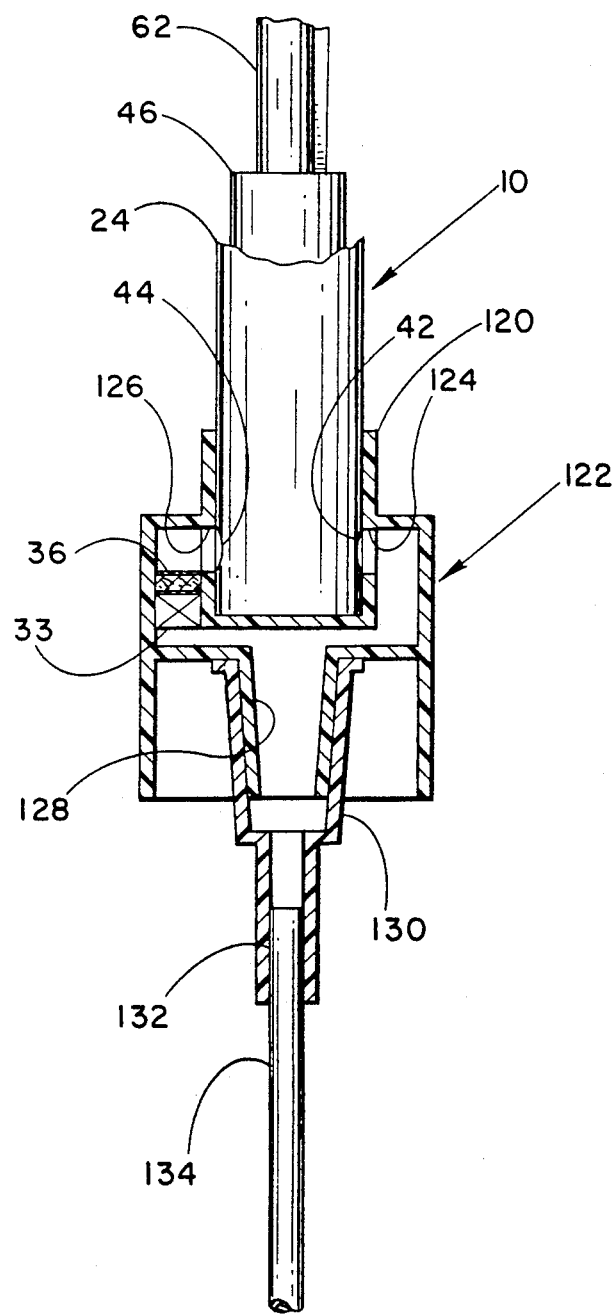

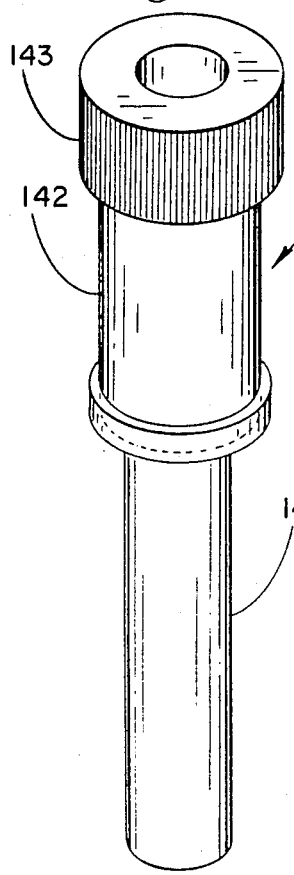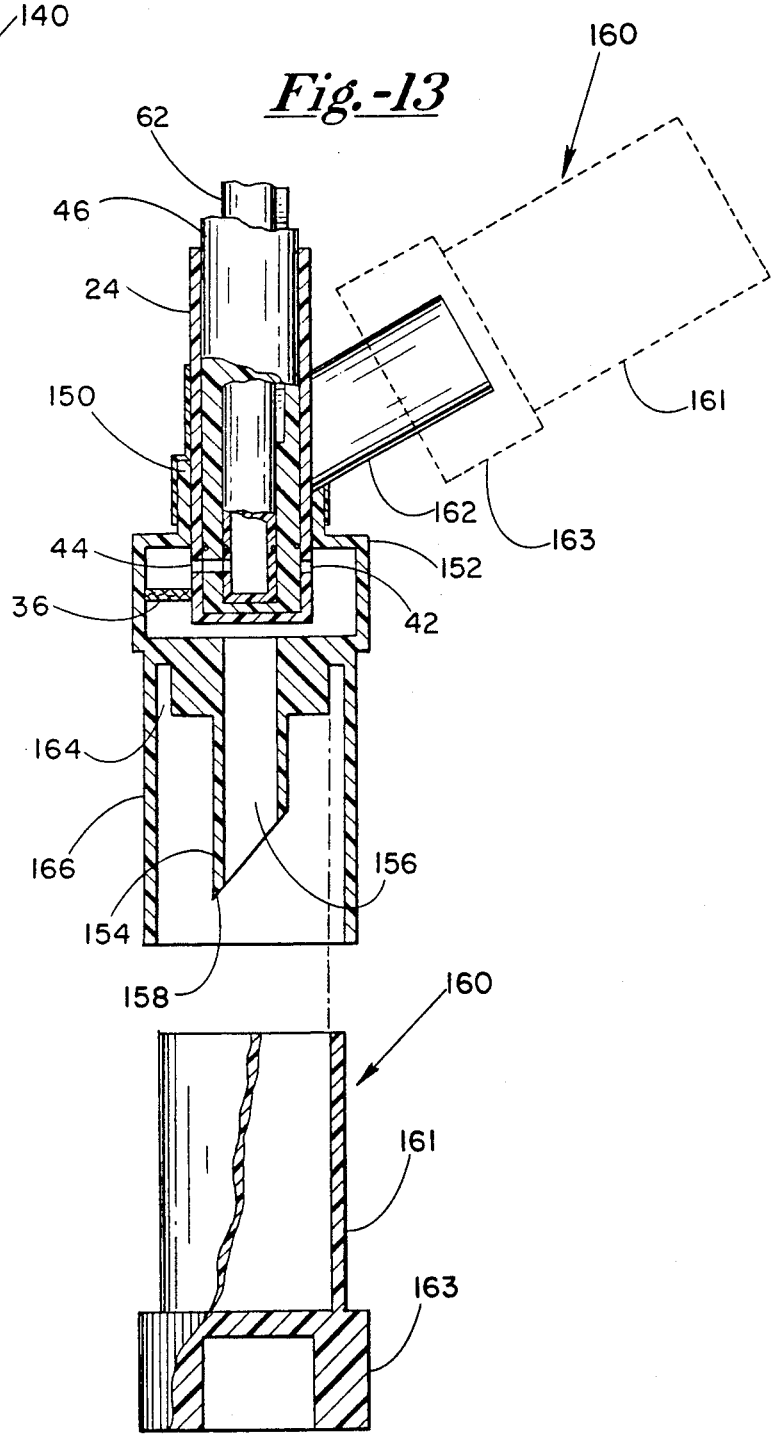

SAFETY I. V. DRUG INTRODUCER SET

BACKGROUND OF THE INVENTION

CROSS-REFERENCE TO RELATED APPLICATIONS

This application is a continuation-in-part of application Ser. No. 07/639,814, filed Jan. 9, 1991 now abandoned, which, in turn, is a continuation-in-part of application Ser. No. 07/470,746, filed Jan. 26, 1989 now abandoned.

I. Field of the Invention

This invention relates generally to apparatus for delivering medications to a patient via an administration set coupled to deliver a primary fluid, such as saline or glucose, to a patient and thus obviating the need for frequent bolus percutaneous injections.

II. Discussion of the Prior Art

As is pointed out in the "Background" in the Schweizer Patent 4,685,910, it is known to deliver supplemental drugs to a patient through a conventional administration set. As is further pointed out there, it has long been known to load a simple hypodermic syringe with a liquid medicament and then inject it into the tubing of an administration set delivering a primary fluid to a patient. Such an administration set commonly includes a bag or bottle of a primary fluid, such as saline or glucose, which is suspended from a stand and connected through medical tubing to an infusion cannula. It is also known in the art to include a self-sealing elastomeric septum in the I.V. line so that secondary fluids, e.g., liquid medicaments, can be injected through the septum using a fine hypodermic needle and when the needle is withdrawn, the self-healing nature of the elastomeric material precludes leakage therethrough.

With concern over the spread of the AIDS and hepatitis viruses, many medical professionals prefer to avoid the use of hypodermic needles in that it frequently happens, through accident, that such professionals or other hospital or clinic personnel may stick themselves with needles that may or may not be contaminated. Because of the unknown nature of the event, severe psychologic strains may occur as well as the need for repeated diagnostic testing over many months. Accordingly, it is the principal object of the present invention to provide a needleless I.V. introducer set whereby medicaments may be introduced into the patient's bloodstream, via an administration set, but where the use of hypodermic needles is obviated.

SUMMARY OF THE INVENTION

In accordance with one embodiment, this object is achieved by providing a molded plastic tubular Tee whose cross-portion is insertable into a tubular I V. line and whose intersecting stem portion includes a female socket for receiving the distal end portion of an outer tubular shaft having a pair of aligned apertures extending through the wall thereof just above a closed distal end of the shaft. Adapted to fit within the lumen of the outer shaft with a predetermined minimal clearance is an inner tubular shaft having a lumen of non-circular cross-section and a single aperture passing through the wall thereof proximate its distal end. The dimensions are such that the aperture in the inner tubular shaft can be aligned with one, the other or neither of the pair of apertures in the outer tubular shaft. Fitted into the non-circular cross-sectional lumen of the inner tubular shaft is a tubular key member whose outer profile corresponds to the non-circular central lumen of the inner tubular shaft. The key member also includes a single aperture which is aligned with the single aperture in the inner tubular shaft when the key is inserted into its lumen. Integrally molded with the proximal end of the key member is a Luer fitting adapted to mate with a corresponding fitting on the end of a conventional plunger-type syringe.

By rotating the key, the aligned apertures of the key and the inner tubular shaft may be juxtaposed relative to an appropriate one of the apertures in the outer tubular member so that when the plunger of the syringe is depressed, a liquid medicament will be transferred from the syringe, through the key member and out through the aperture in the outer tubular shaft and, thence, through the Tee into the primary fluid stream passing therethrough. When the aperture in the inner tubular shaft and stem are rotated out of alignment with the apertures in the outer tubular shaft, the flow of liquid from the syringe to the I.V. line or from the I.V. line back into the syringe is precluded. A particulate filter may be placed in the Tee at a location downstream of the aperture in the outer tubular member to prevent particles greater than a predetermined size from reaching the patient. Also, a system of one-way valves located in the Tee member ensures proper flow of the primary liquid relative to the needleless administration set in different modes of use.

In an alternate embodiment, the outer tubular shaft is simplified to contain a single aperture extending through the wall just above the closed distal end of the shaft. This single aperture can be used for both injection and withdrawal as desired. The system may have a permanent safety shield to preclude the possibility of inadvertent skin puncture, and the shield may be adapted to a plurality of applications.

The apparatus of the present invention further includes a medicament vial piercing probe matable with the distal end portion of the key shaft when the key is removed from the lumen of the inner tubular member whereby the medicament may be drawn from a vial into a syringe coupled to the Luer fitting on the proximal end of the key member.

The kit in which the present invention may be packaged further, for example, might include an antiseptic swab having a frangible vial containing the antiseptic and coupled to the vial is a tubular stem terminating in a cotton ball or sponge. By squeezing the vial, the antiseptic would be released and flow through the tube to saturate the cotton ball. Following that, the swab could be inserted down the lumen of the inner tubular shaft to sterilize the exposed surfaces.

Further features and aspects of the invention will become apparent to those skilled in the art from the following detailed description of a preferred embodiment, especially when considered in conjunction with the accompanying drawings in which like numerals in the several views refer to corresponding parts.

BRIEF DESCRIPTION OF THE DRAWINGS

FIG. 1 is a side elevation of one embodiment of the system of the present invention;

FIG. 2 is a partially sectioned view of the present invention installed in the I.V. line of an administration set.

FIG. 4 is a cross-sectional view of the apparatus of FIG. 3 when in its assembled state;

FIG. 5 is a cross-sectional view taken along the line 5—5 in FIG. 4;

FIG. 5A is a cross-sectional view taken along the line 5—5 when the key member has been rotated 90° from that shown in FIG. 5;

FIG. 8 illustrates a "prep" swab usable with the needleless drug introducer set of the present invention;

FIG. 9 is a partial, sectional view which illustrates an alternative embodiment of the invention;

FIG. 12 depicts a cover assembly for the key member in accordance with the invention;

FIG. 13 is an alternate embodiment of the multi-tube system of FIG. 3 for use as a withdrawal or injection system;

DESCRIPTION OF THE PREFERRED EMBODIMENT

Figure 3:
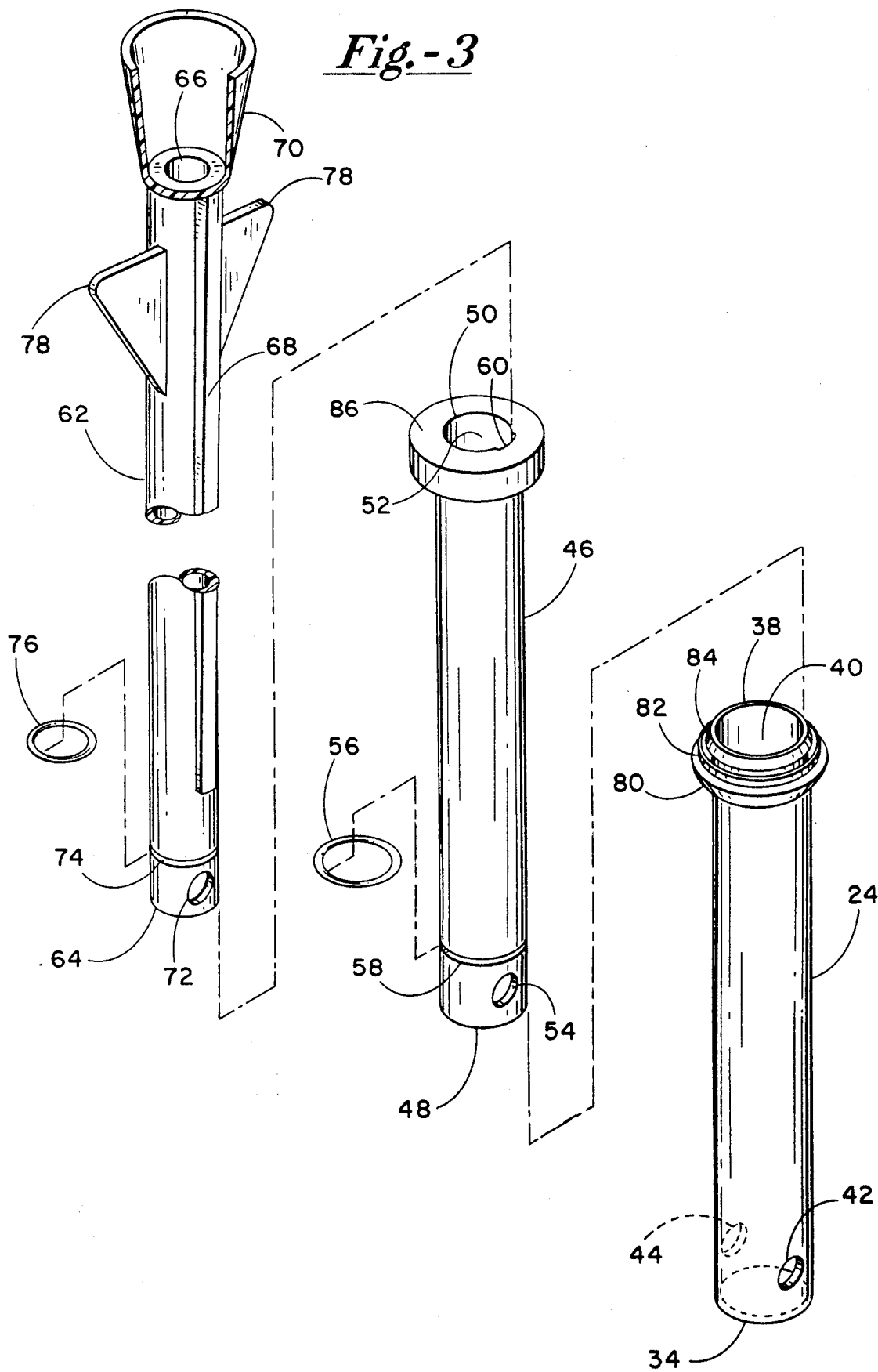
FIG. 3 is an enlarged, blown-apart view of the outer tubular shaft, inner tubular shaft and key member employed in the embodiment of the system of FIG. 1.

Referring first to FIG. 1, there is indicated generally by numeral 10 a needleless I.V. drug introducer set which includes a first flexible plastic tube 12 leading to a supply of the primary liquid, e.g., either saline or a glucose solution, contained in an I.V. bag (not shown). A second length of tubing 14 leads to a cannula (not shown) which penetrates the skin and enters a suitable vein. Intermediate the tubular sections 12 and 14 is a molded plastic tubular Tee member 16 having a cross-portion 18 and a stem portion 20 integrally molded with the cross-portion. Details of the Tee member 16 are shown in the cross-sectional view of FIG. 2.

The stem portion 20 of the Tee 16 includes a cylindrical segment 22 forming a female socket for receiving an outer tubular shaft 24 therein. A tight seal between the collar of socket portion 22 and the exterior surface of the outer shaft 24 may be obtained as by utilizing a short length of shrink-fit tubing 26, or the like, to surround the respective portions, as illustrated, and then applying heat to shrink the tubing into tight conformance with the exterior surfaces of the outer shaft 24 and the cylindrical socket 22.

Fitting within the Tee 16 on the upstream portion of the cross-piece 18 is a check valve 28 which permits the flow of the primary liquid only in the direction indicated by the arrow 30. Likewise, a similar check valve 32 is disposed between the closed distal end 34 of the outer tubular shaft 24 which also permits flow only in the direction of the arrow 30. Positioned within the Tee is a particulate filter 36 which, while allowing the flow of liquids therethrough will block any solid particles which may be present in the flow stream above a predetermined size.

Referring now to the exploded view of FIG. 3, the outer tubular shaft 24 has a proximal end 38, a closed distal end 34 and a lumen 40 of circular cross-section extending between the distal end 34 and the proximal end 38. Disposed a short distance proximal of the distal end of the tubular shaft 24 is a pair of apertures 42-44 which are diametrically opposed from one another. The member 24 is preferably formed from a suitable medical grade plastic in a molding or extruding operation.

Also illustrated in the view of FIG. 3 is an inner tubular shaft 46 in the form of a right circular cylinder whose diameter is slightly less than the diameter of the lumen 40 whereby the shaft 46 may be inserted into the lumen 40 and rotated. The inner tubular shaft 46 includes a closed distal end 48, an open proximal end 50 and a lumen 52 of non-circular cross-section extending between the distal end 48 and the proximal end 50. Disposed immediately above the distal end 48 of the inner shaft 46 is a single aperture, as at 54, which may be brought into alignment with either of the apertures 42 and 44 in the outer tubular shaft as in FIG. 5 or blocked by the inner wall of the outer shaft when halfway in between those apertures as in FIG. 5A. A seal between the exterior of the inner tubular member 46 and the interior wall of the outer tubular member 24 is created, as by using an 0-ring 56 arranged to be disposed in an annular recess 58 formed in the wall of the inner tubular member 46.

With continued reference to FIG. 3, it can be seen that the lumen 52 is generally circular but includes a longitudinal groove 60 extending a predetermined distance along the shaft 46 as a radial extension to the lumen 52.

Adapted to fit within the lumen 52 of the inner tubular shaft 46 is a tubular key member 62 having a closed distal end 64 and an open proximal end 66. A longitudinally extending, radially projecting rib is integrally molded therewith for cooperating with the groove 60 on the inner shaft. Affixed to the proximal end 66 of the key member 62 is a flared Luer fitting 70. An aperture 72 extends through the thickness dimension of the wall near the distal end 64 and is in fluid communication with the internal lumen of the tubular key.

An annular groove 74 is cut in the exterior wall of the key member proximal of the aperture 72 for receiving a 0-ring 76 made from an elastomeric material. Thus, when the key 62 is inserted into the lumen of the inner tubular shaft 46 with the rib 68 fitted into the groove or slot 60, the aperture 72 will be aligned with the aperture 54 and a fluid tight seal is created by the 0-ring to preclude penetration of liquid proximal to the 0-ring. Also projecting radially outward from the exterior of the key 62 are ears 78 which may be engaged by the thumb and forefinger to facilitate rotation of the key 62 about its longitudinal axis.

Referring now to FIG. 4, there is shown a cross-sectional view of the assembly of FIG. 3. This view helps to illustrate the manner in which the inner tubular shaft 46 is locked in place within the bore or lumen 40 of the outer tubular shaft 24. In particular, the outer tubular shaft 24 has, at its proximal end, a flared portion 80. Extending radially and projecting upward from the flared portion is an annular ring 82 and a barb 84. Integrally molded at the proximal end of the inner tubular shaft 46 is an annular ring 86 whose underside is grooved to receive the ring 82 and the barb 84 when the inner tubular shaft 46 is forced down into the lumen 40 of the outer tubular shaft 24.

The cross-sectional views of FIGS. 5 and 5A show the manner in which, by rotating the key member 62, the apertures 54 and 72 may be brought into alignment with the apertures 42 or 44, but between these two positions, the two apertures 54 and 72 are effectively blocked by the wall of the outer tubular sleeve 24. In this regard, reference is again made to FIG. 2. Assuming that the Tee 16 is disposed in a I.V. line, primary fluid will flow in the direction of arrow 30 through the one-way check valves 28 and 32, and through the tubing 12 and a percutaneous cannula (not shown) placed in the patient's vein. While the particulate filter 36 is illustrated in FIG. 2 as being located downstream of the aperture 44, it is apparent that it may be located proximally of the valve but distal of the one-way valve 33. When it is desired to inject a medicament into the patient's blood stream, a syringe, indicated generally by numeral 88 in FIG. 1 and having a Luer fitting 90 surrounding an exit orifice (not shown), may be plugged into the mating Luer fitting 70 on the distal end of the key member 62. By rotating the key so that the aligned apertures 72 and 54 of the key and inner shaft become aligned with port 44 and by depressing the syringe's plunger 92, the medicament will be made to flow through the lumen of the key 62 and a one-way check valve 33 into the cross-portion of Tee 16 where it will mingle with the primary liquid and thus ultimately enter into the patient.

In cases where it is desired to dilute the medicament with the primary fluid, the plunger 92 on the syringe 88 may be drawn back to create a vacuum which will draw the primary liquid through the now-aligned apertures 42, 54 and 72 and the lumen of the key 62 into the syringe. Now, by again rotating the key so as to align the apertures 54 and 72 with the aperture 44 and again depressing the plunger 92, the diluted mixture or solution will be forced through the key and out the aperture 44 through the one-way valve 33 into the primary liquid flow path through the cross-portion 18 of the molded Tee 16.

Figure 10:
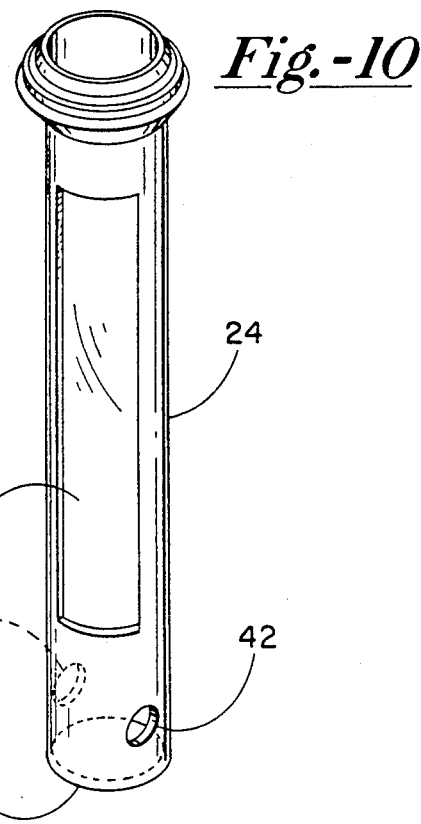
FIG. 10 is an alternate embodiment of the outer tubular shaft of FIG. 3.
Figure 11A:
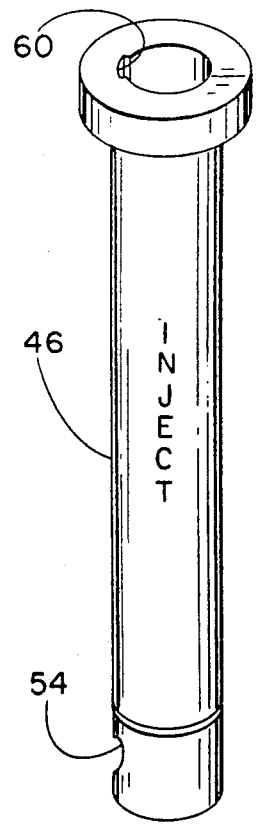
FIGS. 11A, 11B and 11C are rotated views of an alternate embodiment of the inner tubular shaft of FIG. 3 for use with the outer tubular shaft of FIG. 10.
Figure 11B:
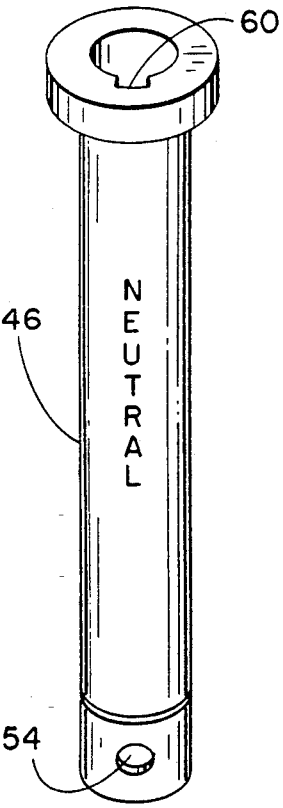
Figure 11C:
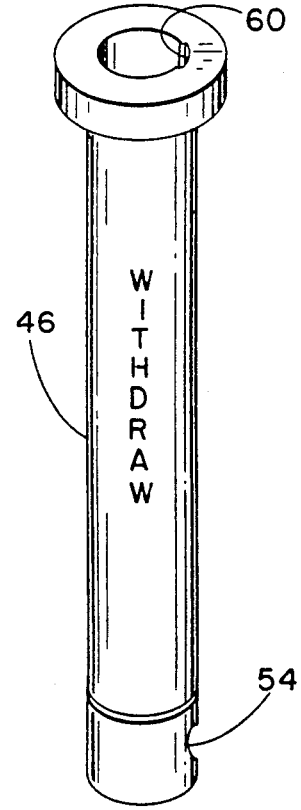

FIG. 10, together with FIGS. 11A–11C illustrate an embodiment of the outer tubular shaft 24 and the inner tubular shaft 46 which include positional indicia to facilitate operation of the device. A transparent section 24A is provided in the outer tubular shaft 24 which aligns with labelling on the inner tubular shaft 46 so that the relative positioning of the opening 54 with respect to the openings 42 and 44 is indicated directly. This, of course, reduces the chance for error in addition to allowing rapid and easy identification of the positional alignment of the device.

Figure 6:
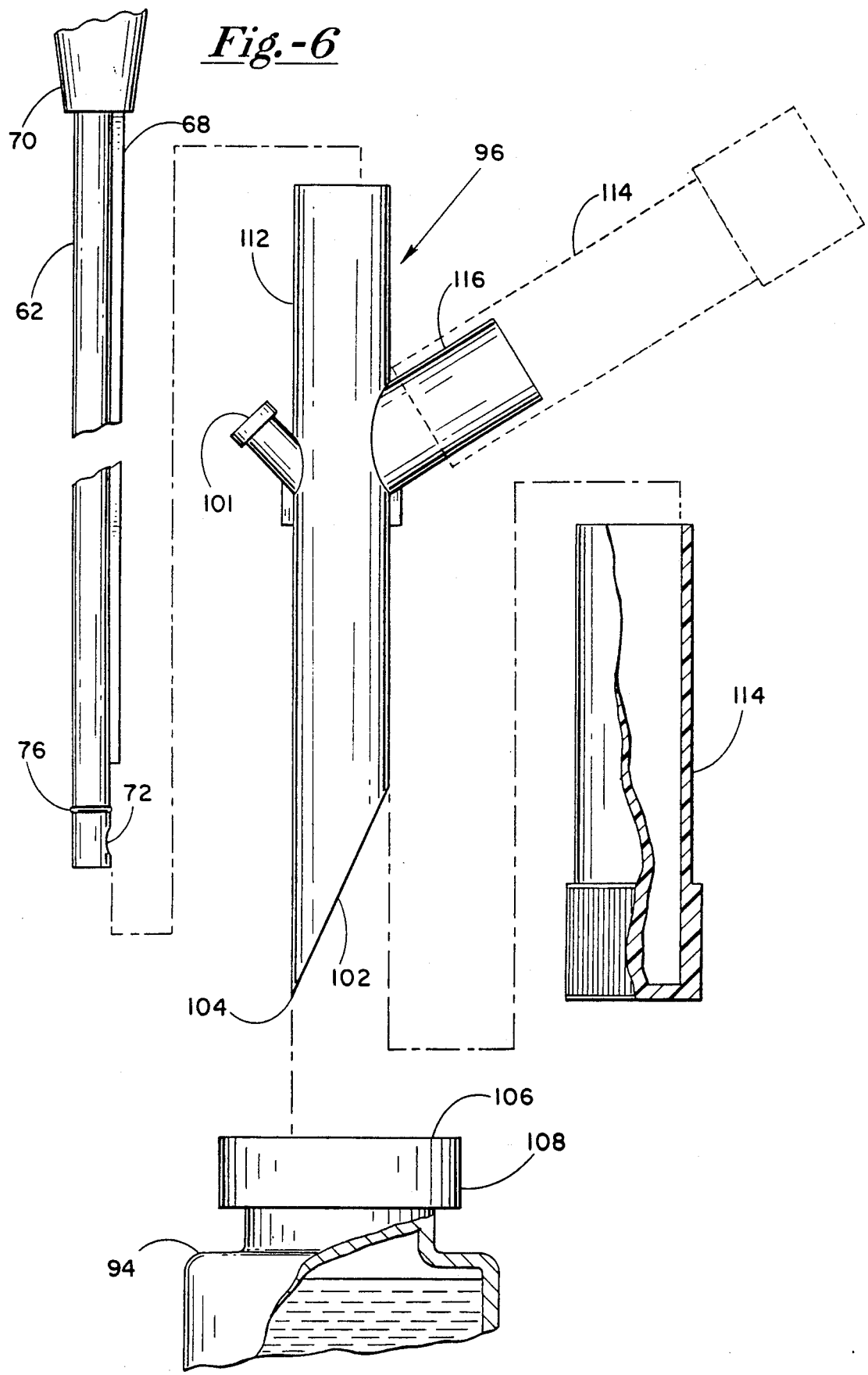
FIG. 6 is an enlarged blown-apart view of a probe member used to access the contents of a medicament vial and its cooperation with the key member of FIG. 3.
Figure 7:
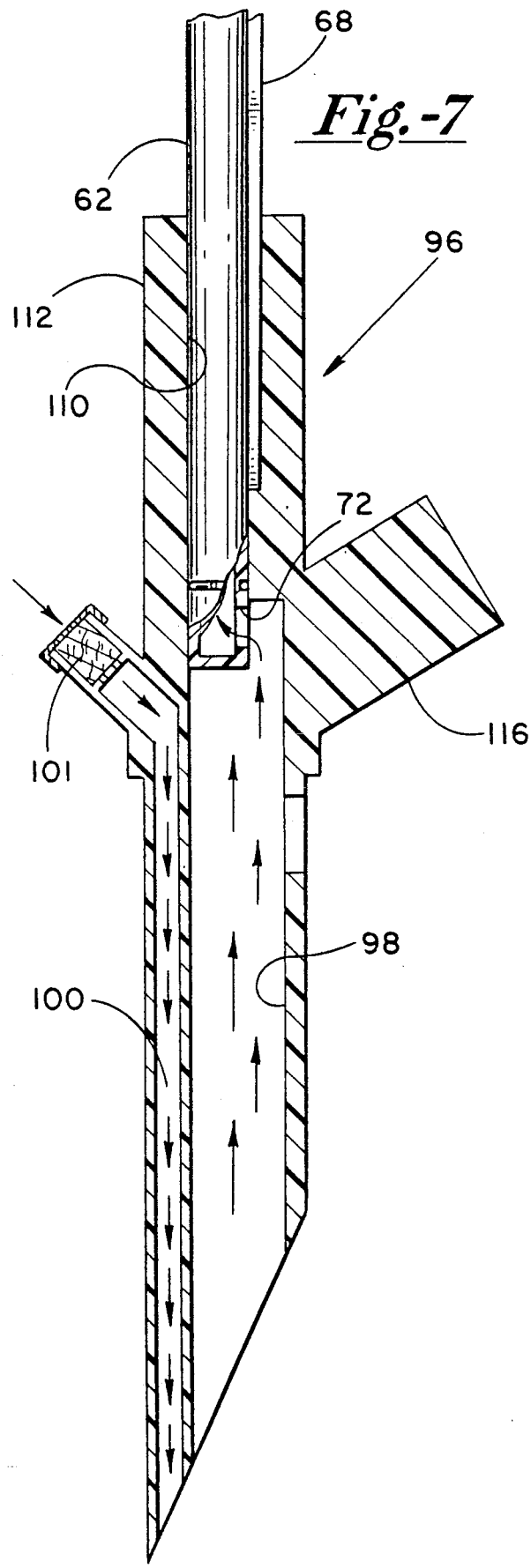
FIG. 7 is a cross-sectional view of the probe of FIG. 6.

To facilitate filling of a syringe, such as 88 in FIG. 1, from a standard medicament vial 94, FIG. 6 illustrates a molded plastic probe or spike 96. As shown in the cross-sectional view of FIG. 7, the spike 96 is a molded plastic part and includes a main lumen 98 for the passage of a liquid therethrough and a second lumen 100 through which make-up air may pass. The spike 96 has a beveled distal end 102 terminating in a point 104 which can be used to pierce the rubber septum 102 terminating in ak point 104 which can be used to pierce the rubber septum 106 on the top 108 of the medicament vial 94. The previously-described key 62 is dimensioned to plug into the tubular bore 110 in the upper molded portion 112 of the spike with the O-ring 76 providing a fluid tight seal between the wall of the bore 110 and the key member 62.

Prior to the insertion of the key member 62 into the lumen of the secondary shaft and rotation of that shaft to its medicament dispensing position, it is advisable to "prep" the exposed surfaces with an appropriate antiseptic to insure sterility. In this regard and with reference to FIG. 8, the prep device indicated generally by numeral 103 preferably includes a reservoir made from a compressible material 105 for containing an antiseptic solution 107. The reservoir or vial 105 includes a frangible diaphragm 109 which will rupture when the compressible reservoir 105 is squeezed. Once broken, the solution 107 may flow through the lumen of a tubular stem 111 to soak a sponge-like element 113 with the antiseptic solution. By stuffing the sponge-like member 113 into the bore of the secondary shaft 46, the antiseptic solution can be applied to the exposed surfaces within the assembly.

A covered container such as that shown in FIG. 12 generally at 140 can be provided to protect the key member 62 and maintain it in a sterile environment prior to first use. Such a container includes a lower hollow portion 141 and a threadably attached cover member 142. Removal is facilitated by the knurled knob.

The lower portion of the spike, including the beveled edge 102, is covered by a tubular cap 114, as indicated in FIG. 6, but still prior to use, the cap is removed and temporarily conveniently held for reuse by slipping its open end over a molded plastic solid stub 116 formed on the upper portion 112 of the spike as indicated by the ghost line representation.

In use, the pointed end 104 of the spike is forced through the elastomeric septum 106 and into the fluid contained within the vial 94. At this time, the "prepped" key member 62 may already have been inserted into the upper end 112 of the spike and a syringe 88 joined to the Luer fitting 70 of the key. Now, when the thus-described assembly is inverted and the plunger 92 on the syringe is drawn back, a vacuum is created causing the medicament in the vial 94 to travel through the lumen 98 of the spike, through the orifice 72 in the key member 62 and thence through the lumen of the key member into the syringe. At the same time, makeup air flows through the filtered inlet port 101 of the lumen 100 and into the vial 94, facilitating the withdrawal of the liquid medicament.

As has already been explained, to now inject the medicament into the primary liquid flow in the administration set, the key member 62, with the filled syringe attached to it, is inserted into the "prepped" bore 52 of the secondary shaft 46 and rotated until its aperture 54 becomes aligned with the aperture 44 on the primary shaft. Now, when the plunger 92 is depressed, the contents of the syringe will be forced out of the syringe, through the lumen of the key and out through the aperture 44 into the primary liquid stream flowing through the cross-portion of the Tee 16. Following the administration of the drug, the key will be turned 90° to again block away any flow of liquid into or out of the key member.

ALTERNATIVE EMBODIMENTS

Where instead of injecting a medicament into an I.V. line 12–14 as illustrated in FIG. 1, with slight modification, the introducer set of the present invention may be used directly with an infusion cannula by a simple modification of the stem portion 20 of the introducer set shown in FIG. 2. Referring to FIG. 9, rather than providing a Tee for introducing into a I.V. line, the primary shaft 24 fits into a cylindrical sleeve 120 in a molded plastic adapter indicated generally by numeral 122. The sleeve or socket 120 includes diametrically opposed apertures 124 and 126 which are positioned so as to be aligned with the apertures 42 and 44 formed in the side walls of the primary shaft 24. As in the embodiment of FIG. 2, the device of FIG. 9 may include a particulate filter 36 downstream of the aperture 44 as well as a one-way valve 33. Centrally disposed within the adapter 122 is a male Luer lock fitting 128 which is adapted to mate with a female fitting 130 affixed to the proximal end 132 of an infusion cannula 134. As with the embodiment of FIGS. 1 through 4, a needleless syringe 92 may be coupled to the proximal end 70 of the key member 62 and when the key is rotated so that apertures 54 and 72 become aligned with the aperture 44, the plunger of the syringe may be depressed to cause the liquid medicament to flow down the lumen of the key 62, through the orifices 44 and 126, through the particulate filter 36 and the one-way valve 33 and from there through the lumen of the infusion cannula 134 into the patent. Rotating the key 90 degrees from the position shown in FIG. 9 results in the aperture 44 being blocked, thereby precluding the back-flow of the patient's blood into the interior of the key 62.

An additional embodiment or modification is shown in FIG. 13. In that embodiment, the primary shaft 24 fits into a cylindrical sleeve or double female socket 150 which forms part of a molded transition member indicated generally by numeral 152. The sleeve or socket 150 further includes a plastic probe or spike 154 which includes a hollow main lumen 156 and a bevelled distal end 158. The spike is provided with a removable protective plastic cover or tubular cap 160 having a tubular portion 161 and a relatively larger diameter solid top 163. The cap can be positioned with its open end over a molded plastic solid stub 162 which may be formed as part of the upper assembly attached to the tube member 24. The cap 160 is designed to fit over the spike 154 in a groove 164 fitting just inside tubular sheath member 166, which, in turn, provides a safety shield for the spike member 154, to provide protection and a clean environment. Upon removal of the tubular cap member 160, the tubular member 166 still shields the spike 154 so that it cannot cause any inadvertent punctures. The tubular member 166, however, is sufficiently large in diameter that the system can be used as a syringe-filling probe in which the spike is used to pierce the rubber septum of a medicament vial, or the like, as in the manner of FIG. 6. The system of FIG. 13, of course, can also be used to inject material as into a direct cannula connected tube in the mode of FIG. 9, into the needleless system of FIGS. 1–3.

FIG. 13 illustrates the system in the injection position with the apertures 54 and 72 aligned with the aperture 44. By rotating the member 62 one-half turn, the system can be aligned with the opening 42 and used to withdraw fluid.

Figure 14:
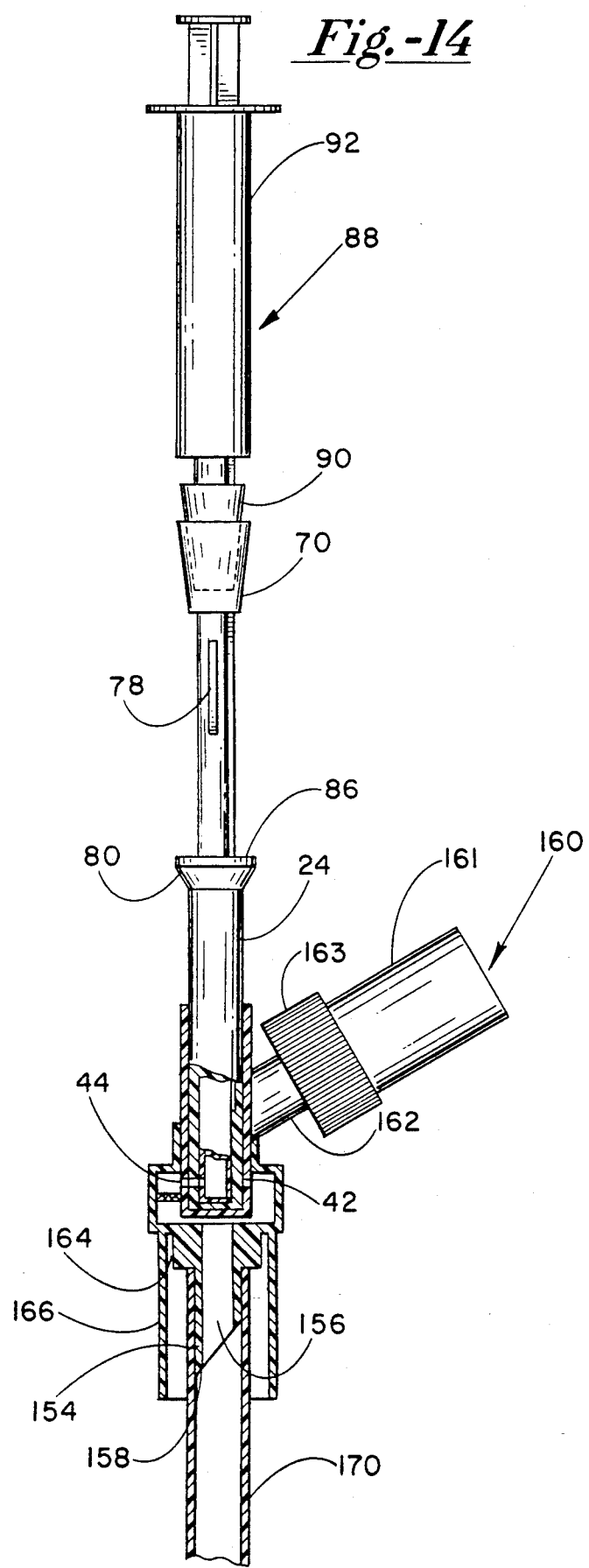
FIG. 14 depicts the embodiment of FIG. 13 for use in an injector mode with attached syringe.
Figure 15:
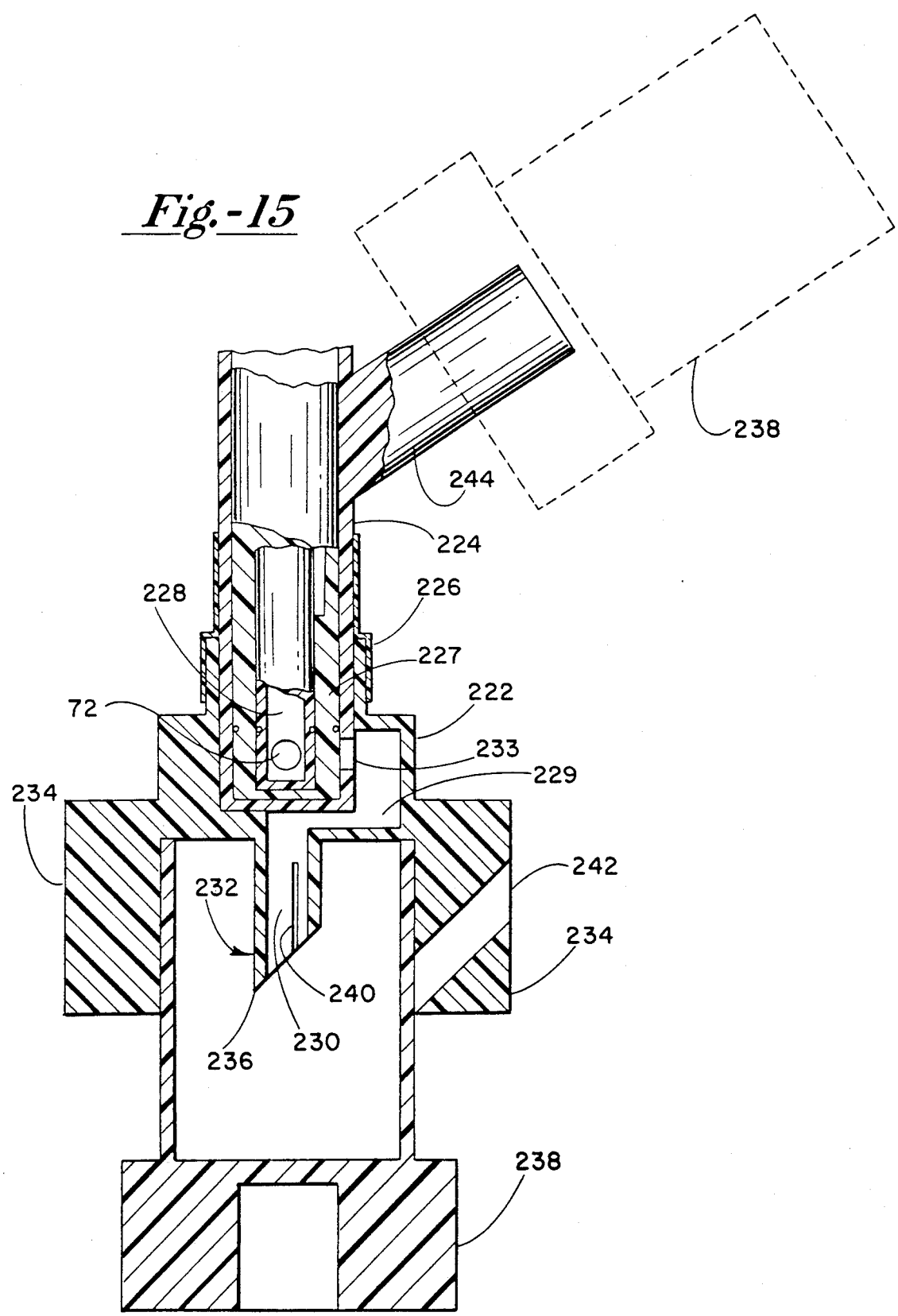
FIG. 15 is a fragmentary view, partially in section, depicting an alternate embodiment of the multi-tube system of FIGS. 1 and 3 for use as a withdrawal or injection system having a single inlet/outlet aperture in the outer tubular member.

FIG. 14 depicts the adoption of the needleless injection system of FIG. 13 in yet another important application in which the spike 154 is fitted into a tubular member 170. The tubular member can be an I.V. port or I.V. tubing such that the contents can be added to an I.V. bag or directly into a fluid conduit connected to an I.V. cannula.

FIGS. 15–19, 20A and 20B depict yet another embodiment of the injection and withdrawal system of the invention in which the key multi-chamber system is simplified to include a single inlet/outlet chamber together with a single-apertured outer tubular member. Thus, the system includes an outer or molded transition member 222 which forms a female socket for receiving an outer tubular member 224 sealed as by a short length of shrink-fit tubing 226. The system also contains an inner tubular member 227 and hollow key member 228 assembled in the manner of the exploded view of FIG. 3. The system describes a single inner hollow chamber 229 which connects a hollow main lumen 230 of a plastic probe or spike member 232 with the interior of the key lumen as aligned with aperture 233 in the manner previously described for other embodiments. A sheath member 234 is provided which extends beyond the tip 236 of the bevelled distal end of the spike member 232 to protect the user from any inadvertent punctures during use of the device. In addition, a movable protective plastic cover or cap 238 is provided which fits into the interior of the sheath 234 to provide an initially sterile environment. The injection barb or spike 232 is further provided with a minute pressure release slot 240 and the sheath 234 may be provided with a further access aperture 242 to accommodate certain uses of the device.

Figure 16:
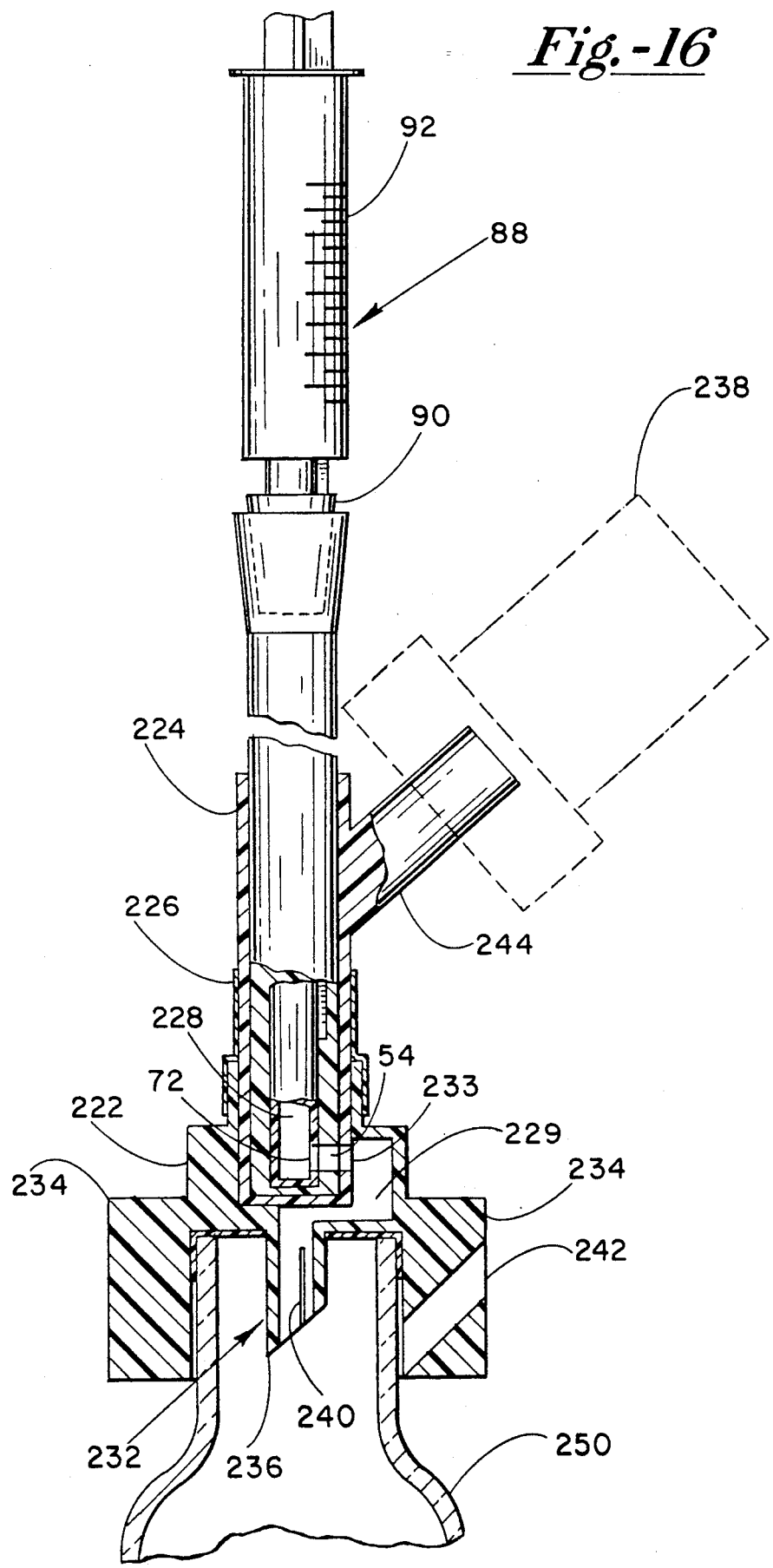
FIG. 16 is a further fragmentary view, partially in section, of the embodiment of FIG. 15 as used to access the contents of a medicament vial.

FIG. 16 illustrates the use of the device for withdrawing a dose of medicine from a standard medicament vial or bottle 250. Note that the keyed system is again rotated to align a cognizant opening 54 thereby connecting the interior lumen of the key member through opening 72 with the chamber 229 and also lumen 230 of the spike 232. The opening 240 in spike member 232 allows displacement of the air from the chamber 229 during filling. It is noted in phantom that the cap 238 may also conveniently be stored atop the stub member 244.

Figure 17:
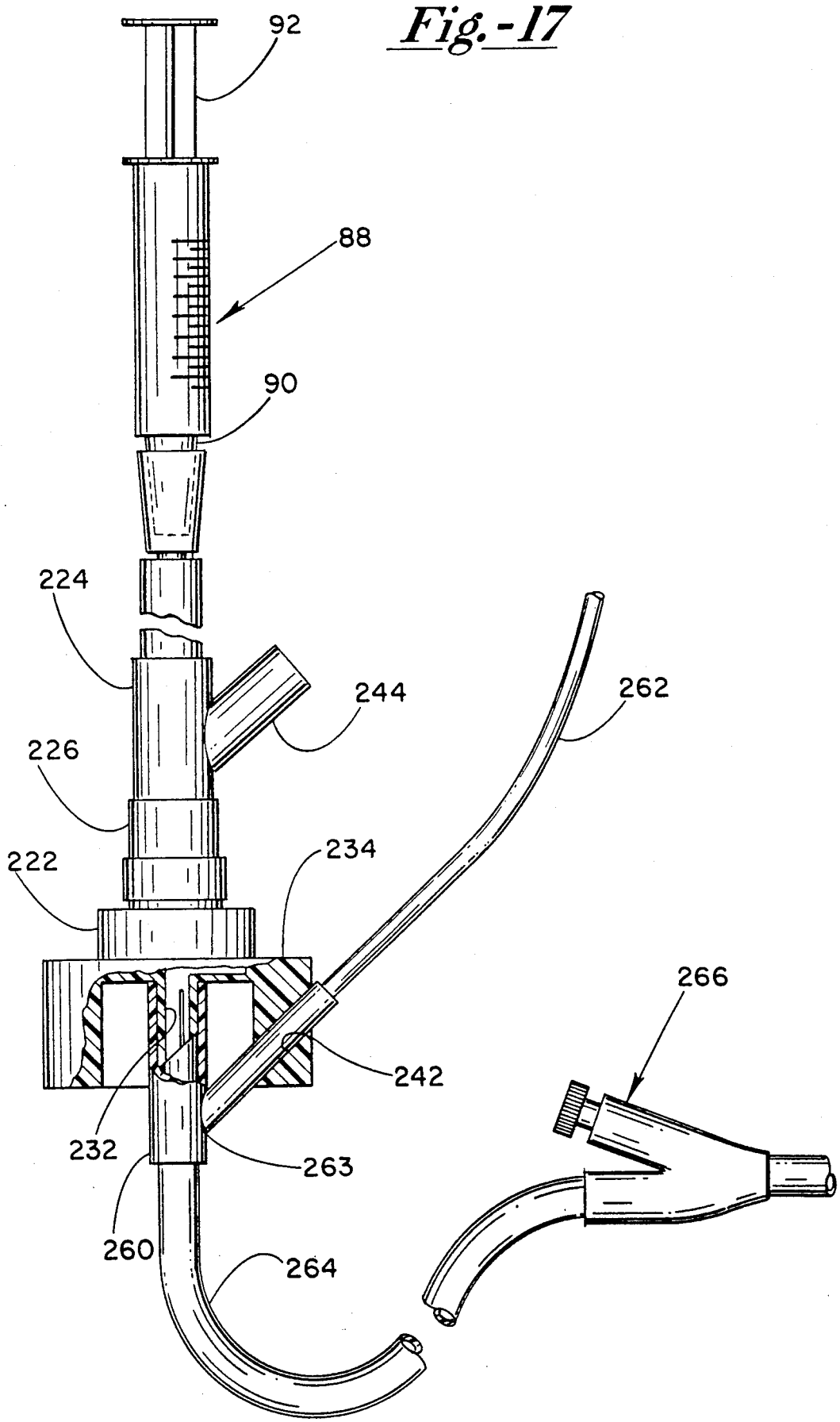
FIG. 17 is a partially cut-away view showing the embodiment of FIG. 15 as used in an injecture mode addressing a branched tubular I.V. system.

FIG. 17 shows the adaptation of this system to direct connection with an I.V. introducer system much a that discussed with regard to the embodiment of FIGS. 1–5. It should be noted that the opening 242 readily allows connection of the sheath member and thus spike member 232 to a normal medicament inlet I.V. configuration including an inlet tube 260 Y-connected to a main gravity fed line 262 at 263 which are then combined at 264 in a well-known manner. An additional Y-connected system is illustrated in the I.V. system at 266. From the figure, it can readily be seen that the identical device can be used both to withdraw a dose from a typical medicament container and administer the dose, or possibly another dose, through a standard I.V. inlet interchangeably, all without the exposure of anyone involved to an open, unprotected needle spike.

Figure 18:
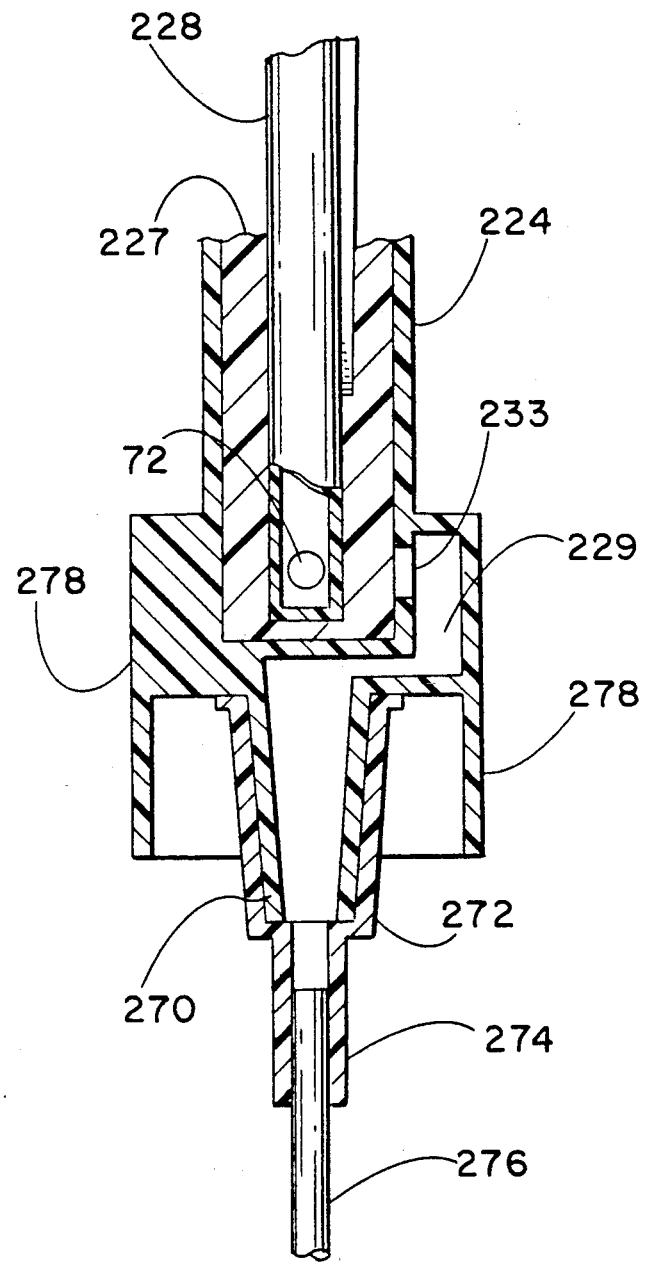
FIG. 18 is a fragmentary view, partially in section, of an alternate embodiment of the device of FIG. 15.

FIG. 18 is an illustration similar to FIG. 9 showing the device provided with a male Luer lock fitting 270 adapted to mate with a female fitting 272 which, in turn, is affixed directly to the proximal end 274 of an infusion cannula 276. The system uses a modified plastic adapter illustrated by 278.

Figure 19:
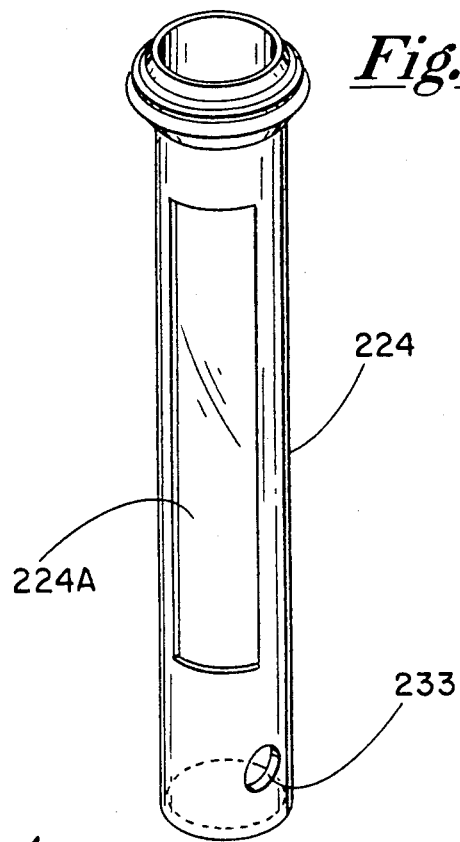
FIG. 19 depicts an alternate embodiment of the outer tubular member of FIG. 15.
Figure 20A:
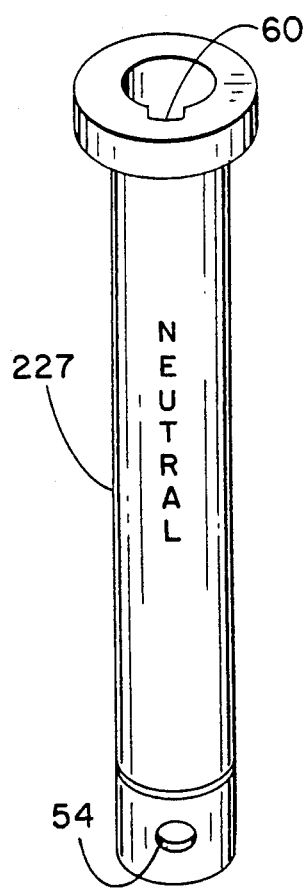
FIGS. 20A and 20B depict rotated views of the inner tubular shaft for use with the outer tubular member of FIG. 19.
Figure 20B:
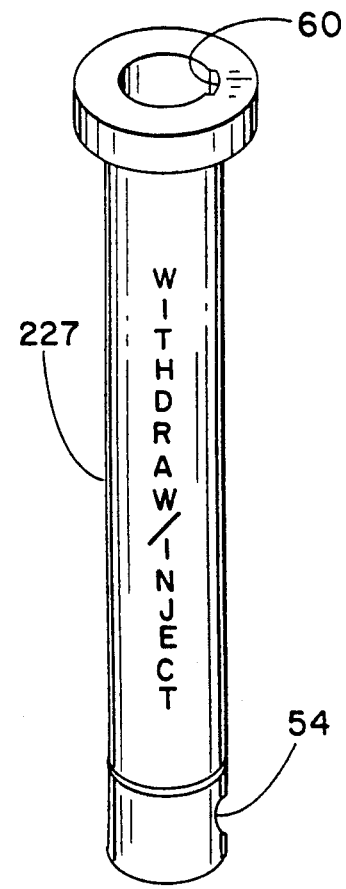

FIGS. 19, 20A and 20B illustrate an embodiment of the outer tubular shaft 224 and the inner tubular shaft 227 with alternative indicia to that shown in FIGS. 11A-11C applicable to the single-hole, two-position system. In this embodiment, the transparent section in the outer tubular member 224 is designated 224A and the available positions simply consist of an injector-/withdrawal position or a neutral or locked position with respect to the alignment of the holes with the chamber 229.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. Apparatus for introducing a medicament into an intravenous line feeding a carrier fluid to a patient of interest comprising:
   (a) a tubular Tee member having a cross-portion insertable into a tubular I.V. line and a stem portion extending generally perpendicular to the cross-portion, the cross-portion connecting upstream and downstream of the stem portion with respect to the normal direction of fluid flow in the intravenous line, the stem portion including a socket means;
   (b) an outer tubular member having a distal portion including a distal end of an outer diameter permitting the distal end to insertably fit into the socket means, the outer tubular member having a central lumen of substantially circular cross-section, an open proximal end, a closed distal end and a pair of apertures spaced radially and positioned essentially equidistant from and proximate the distal end in and extending through the wall of the outer tubular member thereby communicating with the lumen thereof, and with the interior of the tubular Tee member;
   (c) an inner tubular member of substantially circular outer cross-section having an open proximal and a distal end with an outer diameter permitting the inner tubular member to rotatably fit distal end first within the central lumen of the outer tubular member, the inner tubular member having a central lumen of non-circular cross-section including a recessed keyway and a single aperture in and extending through the wall thereof proximate the distal end so as to be rotatably alignable with either of the radially spaced apertures in the outer tubular member; and
   (d) a tubular key member having an outer cross-section corresponding to the cross-section of the central lumen of the inner tubular member and of a size to insertably fit distal end first therein, the key member having a central lumen, an open proximal end, a distal end with a single aperture in and extending through the wall of the tubular key member positioned to be aligned with the aperture in the inner tubular member when the key member is fully inserted into the lumen of the inner tubular member, rotation of the key member further aligning the aperture in the inner tubular member with either aperture in the outer tubular member or and the key member including coupling means at the open proximal end thereof for addressing a medicament dispensing device for receiving the contents thereof.

2. The apparatus of claim 1 and further including means appended to the key member near the proximal end thereof for facilitating the rotation thereof.

3. The apparatus of claim 1 wherein the outer tubular member is positioned in the socket means such that one of the apertures of the pair of apertures in the outer tubular member is disposed upstream relative to the outer with respect to the flow through the cross-portion.

4. The apparatus of claim 3 wherein the pair of apertures in the outer tubular member are diametrically opposed.

5. The apparatus of claim 3 wherein the Tee member includes a first one-way valve means in the cross-portion upstream of the socket means.

6. The apparatus of claim 5 wherein the Tee member further includes a second one-way valve means disposed in the cross-portion of the tubular Tee member between the pair of apertures in the outer tubular member so that the second one-way valve is upstream of one of the pair of apertures in the outer tubular member.

7. The apparatus of claim 6 further including filter means disposed between the aperture downstream of the second one-way valve and the cross-portion at the Tee member.

8. The apparatus of claim 7 wherein the tubular key member is further characterized by position indicating means for directly displaying the relative position of the inner and outer tubular member.

9. The apparatus of claim 1 wherein the Tee member includes a first one-way valve means in the cross-portion upstream of the socket means.

10. The apparatus of claim 1 wherein the outer cross section of the key member includes a longitudinally extending key having a cross-section which corresponds to the keyway in the wall of the inner tubular member.

11. The apparatus of claim 1 and further including tubular probe means connectable to the distal end portion of the tubular key member and adapted to receive liquid from a vial, the tubular probe means including first and second lumens and a pointed distal end.

12. The apparatus of claim 11 wherein the first lumen of the probe allows the flow of liquid medicament therethrough from a vial into the key member and the second lumen allows the flow of replacement air into a vial.

13. The apparatus of claim 1 wherein the tubular key member is further characterized by position indicating means for directly displaying the relative position of the inner and outer tubular member.

14. The apparatus of claim 1 further comprising sterile container means for storing the tubular key member prior to use.

15. Apparatus for introducing a medicament or other fluid of interest into a device connected to an intravenous line or an intravenous device for administering a fluid to or withdrawing a fluid from a patient of interest comprising:
 (a) a tubular transition adapter having a hollow interior volume configured to connect a medicament fluid introducing apparatus into a tubular I.V. line or a device is communication with an I.V. line, the member including a generally cylindrical socket member having a closed bottom, open top and a sidewall, a pair of apertures in the sidewall in communication with the hollow interior volume, spaced radially apart and essentially equidistant from the bottom thereof, a hollow tubular connection member having a first end connected to the hollow interior volume of the transition adapter;
 (b) an outer tubular member with an outer diameter adapted to insertably fit into the socket member, the outer tubular member having a central lumen of substantially circular cross-section, an open proximal end, a closed distal end and a pair of apertures spaced radially in and extending through the wall of the outer tubular shaft into and communicating with the lumen thereof, and with the interior of the tubular transition through the apertures in the socket member, the apertures being positioned essentially equidistant from and just proximal of the distal end of the outer tubular shaft;
 (c) an inner tubular shaft member of substantially circular outer cross-section having an open proximal end and a distal end with an outer diameter adapted to rotatably fit within the central lumen of the outer tubular shaft, the inner tubular shaft having a central lumen of non-circular cross-section including a recessed keyway and a single aperture in and extending through the wall thereof, positioned proximate the distal end so as to be rotatably alignable with either of the apertures in the outer tubular member; and
 (d) a tubular key member having an outer cross-section corresponding to the cross-section of the central lumen of the inner tubular shaft member and of a size to insertably fit therein, the key member having an open proximal end, a distal end and a single aperture positioned to be aligned with the aperture in the inner tubular member when the key member is fully inserted into the lumen of the inner tubular member, rotation of the key member further aligning the aperture in the inner tubular member with an aperture in the outer tubular member or misaligning the aperture in the inner tubular member by disposing it between the apertures in the outer tubular member thereby closing off access to either aperture in the outer tubular member, the key member including coupling means at the open proximal end thereof for addressing a medicament dispensing device for receiving the contents thereof.

16. The apparatus of claim 15 wherein the transition member further comprises a tubular Tee member having a cross-portion insertable into a tubular I.V. line and a stem portion extending generally perpendicular to the cross-portion the stem portion including the cylindrical socket.

17. The apparatus of claim 15 wherein the hollow tubular connection member is further provided with outlet means adapted to receive a connecting tube for connection as to an I.V. system, infusion cannula or other device for administering a fluid to or withdrawing a fluid from a patient.

18. The apparatus of claim 15 further comprising a one-way valve means between one of the apertures in the socket member and the hollow tubular connection member.

19. The apparatus of claim 15 further including a filter means disposed between one of the apertures in the socket member and the hollow tubular connection member.

20. The apparatus of claim 15 further comprising a one-way valve means and filter means disposed between one of the apertures in the socket member and the hollow tubular connection member such that fluid causes to pass through either aperture in the outer tubular member is caused to traverse both the filter and the one-way valve means.

21. The apparatus of claim 15 wherein the tubular connection member of the transition member further comprises:
 (a) a hollow spike member having a beveled distal end and a lumen in fluid communication with the hollow interior volume of the tubular transition member;
 (b) a tubular protective sheath member surrounding the spike member at a distance therefrom and extending a distance beyond the distal end thereof; and
 (c) a common base attaching the tubular sheath member and the spike member to the tubular transition member.

22. The apparatus of claim 21 further comprising cap means including a manipulation section attached to a tubular shaft insertable into the sheath member and surrounding the spike member to thereby seal the spike member from the environment when the tubular shaft of the cap member is inserted.

23. The apparatus of claim 21 further comprising filter means disposed between an aperture of the socket member and the lumen of the spike member.

24. The apparatus of claim 23 further comprising cap means including a manipulation section attached to a tubular shaft insertable into the sheath member and surrounding the spike member to thereby seal the spike member from the environment when the tubular shaft of the cap member is inserted.

25. The apparatus of claim 15 wherein the tubular key member is further characterized by position indicating means for directly displaying the relative position of the inner and outer tubular member.

26. The apparatus of claim 15 further comprising sterile container means for storing the tubular key member prior to use.

27. Apparatus for introducing a medicament or other fluid of interest into a device connected to an intravenous line or an intravenous device administering a carrier fluid to a patient of interest comprising:
 (a) a tubular transition adapter means having a generally hollow interior configured to connect a medicament fluid introducing apparatus into a tubular I.V. line or a device in communication with an I.V. line, the adapter means including at least a first socket means;
 (b) an outer tubular shaft having an outer diameter the distal end of which is adapted to insertably fit into the first socket means, the outer tubular shaft having a central lumen of substantially circular cross-section, an open proximal end, a closed distal end and a single aperture connecting the lumen thereof with the interior of the tubular transition adapter means, the aperture being positioned just proximal of the distal end of the outer tubular shaft;

(c) an inner tubular shaft of substantially circular outer cross-section with an outer diameter adapted to rotatably fit within the central lumen of the outer tubular shaft, the inner tubular shaft having a central lumen of non-circular cross-section including a recessed keyway, an open proximal end and a distal end with a single aperture in and extending through the wall of the inner tubular shaft, communicating with the lumen, the aperture being positioned just proximal of the distal end of the inner tubular shaft so as to be rotatably alignable with the single aperture in the outer tubular shaft; and (d) a tubular key member having an outer cross-section corresponding to the cross-section of the central lumen of the inner tubular shaft and of a size to insertably fit therein, the key member having an open proximal end, a distal end and a single aperture just proximal of the distal end thereof positioned to be aligned with the aperture in the inner tubular shaft when the key member is fully inserted into the lumen of the inner tubular shaft, rotation of the key member further aligning the aperture in the inner tubular shaft with the aperture in the outer tubular member or misaligning the aperture in the inner tubular shaft by disposing it between the apertures in the outer tubular shaft thereby closing off access to either aperture in the outer tubular shaft.

28. The apparatus of claim 27 wherein the key member includes coupling means at the open proximal end thereof for addressing a medicament dispensing device for receiving the contents thereof.

29. The apparatus of claim 27 wherein the transition adapter means further comprises an outlet tube adapted to receive the proximal end of an infusion cannula.

30. The apparatus of claim 27 wherein the transition adapter means further comprises a connection opening oppositely disposed with respect to the socket means, further comprising:

(a) a hollow spike member connected to the opening having a beveled distal end and a lumen in fluid communication with the hollow interior of the transition adapter means;

(b) a tubular protective sheath member surrounding the spike member at a distance therefrom and extending a distance beyond the distal end thereof; and (c) a common base attaching the tubular sheath member and the spike member to the transition adapter means.

31. The apparatus of claim 30 further comprising cap means including a manipulation section attached to a tubular shaft insertable into the sheath member and surrounding the spike member to thereby seal the spike member from the environment when the tubular shaft of the cap member is inserted.

32. The apparatus of claim 30 wherein the tubular key member is further characterized by position indicating means for directly displaying the relative position of the inner and outer tubular shafts.

33. The apparatus of claim 30 wherein the sheath is further provided with an opening for connection with a Y-connected I.V. infusion system.

34. The apparatus of claim 27 wherein the tubular key member is further characterized by position indicating means for directly displaying the relative position of the inner and outer tubular shafts.

* * * * *

UNITED STATES PATENT AND TRADEMARK OFFICE
CERTIFICATE OF CORRECTION

PATENT NO. : 5 169 385
DATED : December 8, 1992
INVENTOR(S) : Christopher J. Turnbull It is certified that error appears in the above-identified patent and that said Letters Patent is hereby corrected as shown below:

In column 10, line 7, delete "and", and insert -- misaligning the aperture in the inner tubular member by disposing it between the apertures in the outer tubular member thereby closing off access to either aperture in the outer tubular member -- .

In column 10, line 19, delete "outer" and insert -- other -- .

In column 11, line 57, cancel claim 16.

Signed and Sealed this

Second Day of November, 1993

Attest:

BRUCE LEHMAN

*Attesting Officer*  Commissioner of Patents and Trademarks